United States Patent
Blainey et al.

(10) Patent No.: US 10,981,167 B2
(45) Date of Patent: Apr. 20, 2021

(54) MASSIVELY PARALLEL ON-CHIP COALESCENCE OF MICROEMULSIONS

(71) Applicants: THE BROAD INSTITUTE, INC., Cambridge, MA (US); MASSACHUSETTS INSTITUTE OF TECHNOLOGY, Cambridge, MA (US)

(72) Inventors: Paul Blainey, Cambridge, MA (US); Anthony Kulesa, Cambridge, MA (US); Jared Kehe, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 15/559,381

(22) PCT Filed: Mar. 18, 2016

(86) PCT No.: PCT/US2016/023245
§ 371 (c)(1),
(2) Date: Sep. 18, 2017

(87) PCT Pub. No.: WO2016/149661
PCT Pub. Date: Sep. 22, 2016

(65) Prior Publication Data
US 2018/0071738 A1 Mar. 15, 2018

Related U.S. Application Data

(60) Provisional application No. 62/135,063, filed on Mar. 18, 2015.

(51) Int. Cl.
*B01L 3/00* (2006.01)
*B01J 19/00* (2006.01)
*B01L 9/00* (2006.01)
*C12N 15/10* (2006.01)
*C12Q 1/18* (2006.01)
*G01N 33/533* (2006.01)
(Continued)

(52) U.S. Cl.
CPC ..... *B01L 3/502784* (2013.01); *B01J 19/0046* (2013.01); *B01L 3/502715* (2013.01); *B01L 3/502761* (2013.01); *B01L 9/50* (2013.01); *C12N 15/1065* (2013.01); *C12Q 1/18* (2013.01); *G01N 33/533* (2013.01); *G01N 33/6845* (2013.01); *B01J 2219/0065* (2013.01); *B01J 2219/00317* (2013.01); *B01J 2219/00418* (2013.01); *B01J 2219/00479* (2013.01); *B01J 2219/00545* (2013.01); *B01J 2219/00547* (2013.01); *B01J 2219/00576* (2013.01); *B01L 7/52* (2013.01); *B01L 2200/025* (2013.01); *B01L 2200/0652* (2013.01); *B01L 2200/0673* (2013.01); *B01L 2200/0689* (2013.01); *B01L 2300/021* (2013.01); *B01L 2300/0654* (2013.01); *B01L 2300/0819* (2013.01); *B01L 2300/0829* (2013.01); *B01L 2300/0867* (2013.01); *B01L 2300/0887* (2013.01); *B01L 2400/046* (2013.01); *B01L 2400/0469* (2013.01); *C40B 50/10* (2013.01); *C40B 60/08* (2013.01); *G01N 2333/195* (2013.01)

(58) Field of Classification Search
None
See application file for complete search history.

(56) References Cited

U.S. PATENT DOCUMENTS

| 2002/0179835 | A1 | 12/2002 | Feygin | |
| 2004/0101912 | A1* | 5/2004 | Rubin | B82Y 5/00 435/7.2 |

(Continued)

FOREIGN PATENT DOCUMENTS

| WO | 2014028537 A1 | 2/2014 | |
| WO | WO-2014028378 A2 * | 2/2014 | ......... B01F 13/0076 |

OTHER PUBLICATIONS

International Search Report and Written Opinion for PCT International Patent Application No. PCT/US2016/023245, dated Jun. 10, 2016, 17 pages.

(Continued)

*Primary Examiner* — Sahana S Kaup
(74) *Attorney, Agent, or Firm* — Johnson, Marcou, Isaacs & Nix, LLC; F. Brent Nix, Esq.; Rachel D. Rutledge, Esq.

(57) ABSTRACT

Embodiments disclosed herein are directed to microfluidic devices that allow for scalable on-chip screening of combinatorial libraries and methods of use thereof. Droplets comprising individual molecular species to be screened are loaded onto the microfluidic device. The droplets are labeled by methods known in the art, including but not limited to barcoding, such that the molecular species in each droplet can be uniquely identified. The device randomly sorts the droplets into individual microwells of an array of microwells designed to hold a certain number of individual droplets in order to derive combinations of the various molecular species. The paired droplets are then merged in parallel to form merged droplets in each microwell, thereby avoiding issues associated with single stream merging. Each microwell is then scanned, e.g., using microscopy, such as high content imaging microscopy, to detect the optical labels, thereby identifying the combination of molecular species in each microwell.

12 Claims, 20 Drawing Sheets

(51) Int. Cl.
*G01N 33/68* (2006.01)
*B01L 7/00* (2006.01)
*C40B 60/08* (2006.01)
*C40B 50/10* (2006.01)

(56) References Cited

U.S. PATENT DOCUMENTS

| | | |
|---|---|---|
| 2009/0203126 A1 | 8/2009 | Hung et al. |
| 2011/0092376 A1* | 4/2011 | Colston, Jr. ............ B01F 3/0807 506/7 |
| 2011/0190146 A1* | 8/2011 | Boehm .................. B01L 7/525 506/7 |
| 2011/0259742 A1* | 10/2011 | Li ..................... B01L 3/502784 204/451 |
| 2013/0210639 A1 | 8/2013 | Link et al. |
| 2014/0045254 A1* | 2/2014 | Tseng ..................... C12M 25/06 435/289.1 |
| 2014/0378349 A1 | 12/2014 | Hindson et al. |

OTHER PUBLICATIONS

Bernal, et al., "Antibiotic Adjuvants: Identification and Clinical Use", Microbial Biotechnology, vol. 6, No. 5, 2013, pp. 445-449.
"International Preliminary Report on Patentability as cited in International Application No. PCT/US2016/023245", dated Sep. 19, 2017, 1-10.
Bernal, et al., "Antibiotic adjuvants: identification and clinical use", Microbiol Biotechnology, vol. 6, No. 5, Feb. 28, 2013, 5 pages.
Campbell, "Supplementary European Search Report for EP16765859.0", dated Sep. 26, 2018, 10 pages.
"Communication pursuant to Article 94(3) EPC issued in EP Application No. 16765859.0", dated Jul. 16, 2019.
"Examination Report issued in EP16765859.0, filed,", dated Feb. 7, 2020, 4 pages.

* cited by examiner

A

B

MASSIVELY PARALLEL ON-CHIP COALESCENCE OF MICROEMULSIONS

CROSS-REFERENCE TO RELATED APPLICATIONS

The present application is a 35 U.S.C. § 371 national stage application of International Patent Application No. PCT/US2016/023245 filed on Mar. 18, 2016, which claims the benefit of U.S. Provisional Patent Application No. 62/135,063 filed Mar. 18, 2015. The entire contents of the above-referenced applications are hereby fully incorporated herein.

TECHNICAL FIELD

The subject matter disclosed herein is generally related to microfluidic devices and methods of using the same. Specifically, the microfluidic devices disclosed herein allow for readily scalable combinatorial screening.

BACKGROUND

Drug and genetic screens, for example, often require the screening of large combinatorial spaces. There is a need for increasingly powerful and scalable methods for searching these vast combinatorial spaces that can otherwise be prohibitive to discovery. Droplets formed on a microfluidic device enable the manipulation of volumes equal to or exceeding the capacity of well-plates, such as 96 and 384 well-plates. However, current strategies for screening combinatorial libraries comprise merging droplets comprising different molecular species using a single-stream approach. When working at the scale of complex combinatorial screening suitable for pharmaceutical screening, a single clog can disrupt and ruin an entire experimental run. Therefore, what is needed are more robust and scalable methods for merging multiple droplets for combinatorial screens of various molecular species.

SUMMARY

In one aspect, the embodiments described herein are directed to microfluidic devices comprising at least one droplet input for receiving one or more sets of droplets, and an array of microwells for randomly receiving two or more droplets from the one or more set of droplets. The microfluidic device may further comprise one or more flow channels, the one or more flow channels allowing droplets from each droplet set to be randomly distributed to a microwell in the array of microwells. In certain example embodiments, the microfluidic device further comprises a loading mechanism comprising a top clamp and a bottom clamp and one or more removeable spacers. The microfluidic device is placed on the bottom clamp. When inserted, the removeable spacers define the one or more flow channels beneath the array of microwells. The top clamp is secured to the bottom clamp by one or more connectors. In certain example embodiments, the one or more connectors are magnets.

In another aspect, the embodiments described herein are directed to a system comprising the microfluidic devices comprising the array of microwells and an automated high content imaging device to image each microwell.

In another aspect, the embodiments described herein are directed to methods of combinatorial screening comprising generating at least one set of drops from a set of molecular species to be screened. The at least one set of drops are then randomly distributed on a microfluidic device comprising an array of microwells. The droplets are distributed via a flow channel running beneath the array of microwells such that droplets are able to rise out of a carrier oil via buoyancy and into an available microwell space. The droplets are then merged in parallel in each microwell to form single merged droplets comprising the combination of molecular species previously contained in each individual droplet. Prior to loading the droplets onto the microfluidic device comprising an array of microwells, the droplets may be barcoded using an optical barcode. The optical barcode identifies the molecular species contained in each drop. In certain example embodiments, the droplets may further comprise a reporter agent to facilitate screening of a particular activity of the combined molecular species.

In another aspect, the embodiments described herein are directed to methods of screening antibiotic and adjuvant pairs. A first set of droplets is generated, each droplet in the first set of droplets comprising an antibiotic to be screened. A second set of droplets is also generated, each droplet in the second set of droplets comprising an adjuvant to be screened. In certain example embodiments, each droplet in the first set of droplets may further comprise an optical barcode identifying the antibiotic and/or antibiotic concentration in each droplet. In certain example embodiments, each second set of droplets may also further comprise an optical barcode identifying the adjuvant and/or adjuvant concentration in each droplet. In certain example embodiments, the second set of droplets may further comprise a reporter bacteria. The reporter bacteria may comprise a nucleic acid construct encoding an optically detectable reporter molecule. The first and second set of droplets are then randomly distributed on a microfluidic device comprising an array of microwells. The droplets are distributed via a flow channel running beneath the array of microwells such that droplets rise out of a carrier oil via buoyancy and into available microwells spaces. The droplets are then merged in parallel in each microwell to form single merged droplets comprising the combination of molecular species previously contained in each individual droplet. Each microwell may then be optically scanned to identify the combination of antibiotic and adjuvant in each microwell via the optical barcode. Likewise, a phenotypic readout may also be obtained by measuring the reporter agent.

These and other aspects, objects, features, and advantages of the example embodiments will become apparent to those having ordinary skill in the art upon consideration of the following detailed description of illustrated example embodiments.

DETAILED DESCRIPTION OF THE EXAMPLE EMBODIMENTS

Overview

Embodiments disclosed herein are directed to microfluidic devices that allow for scalable on-chip screening of combinatorial libraries and methods of use thereof. Droplets comprising individual molecular species to be screened are loaded onto the microfluidic device. The droplets are labeled by methods known in the art, including but not limited to barcoding, such that the molecular species in each droplet can be uniquely identified. The device randomly sorts the droplets into individual microwells of an array of microwells designed to hold a certain number of individual droplets in order to derive combinations of the various molecular species. The paired droplets are then merged in parallel to form merged droplets in each microwell, thereby avoiding issues associated with single stream merging. Each microwell is then scanned, e.g., using microscopy, such as high content imaging microscopy, to detect the optical labels, thereby identifying the combination of molecular species in each microwell. The droplets may further comprise a reporter system, such as cell expressing a fluorescent biomarker or a protein or chemical tag comprising or recognized by (binding to, such as a labeled antibody or bead) an optical marker, to facilitate simultaneous optical phenotyping with molecular species identification.

Microfluidic Devices

Figure 2:
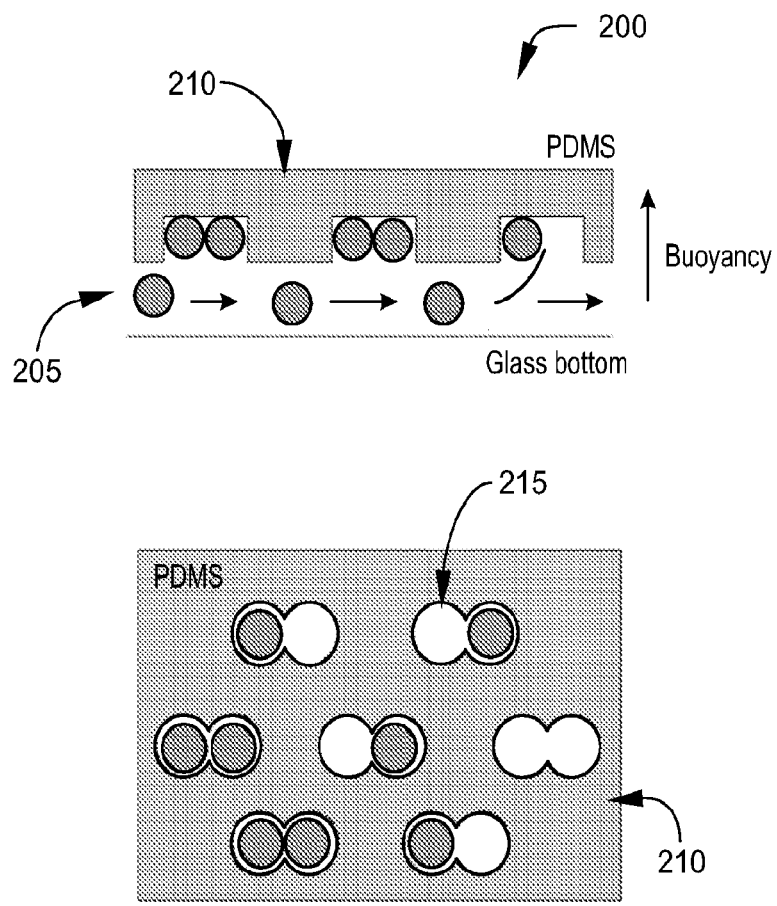
FIG. 2 is a diagram depicting a microfluidic device used to randomly merge pairs of droplets, in accordance with certain example embodiments.

Referring to FIG. 2, in one aspect, the embodiments disclosed herein are directed to microfluidic devices 200 with at least one droplet input 215 (See FIG. 3), at least one flow channel 205, and an array of microwells 215. Droplets comprising different molecular species are generated and loaded onto the device. The droplets may be formed off chip and then loaded via a droplet input 215 onto the microfluidic device comprising the array of microwells. Alternatively, the microfluidic device may be connected directly to a second microfluidic device for forming droplets, which then feeds the formed droplets onto the microfluidic devices comprising the array of microwells via a droplet input 215. In certain example embodiments the microfluidic devices disclosed herein may form a module that is combined with other modules on a single chip. For example, a chip may comprise a droplet formation module and the devices disclosed herein may form a droplet merge module. In one embodiment, the droplets are formed in the droplet formation module and then input into the one or more flow channels of the droplet merge module. The formed droplets are then distributed across one or more flow channels of the microfluidic device for delivery to the microwells.

In certain example embodiments, the device comprises a single flow channel. In certain other example embodiments, the device comprises two or more flow channels. In one embodiment, the one or more flow channels are defined on a bottom layer or a top layer of the device. The flow channel may be an integral part of a device that is formed from the same mold used to define the array of microarrays. Alternatively, the flow channel may be formed by mounting the array of microwells to a solid substrate, such as a glass substrate. In certain example embodiments, a thin space may be inserted between the microfluidic device and the solid substrate to define the one or more flow channels. After loading droplets into the microwells, the spacers may be removed to completely seal the microfluidic device to the solid substrate. Droplets rise or sink via buoyancy from the one or more flow channels into empty microwell spaces.

Each flow channel 205 may have a width of approximately 5 mm to approximately 75 mm; approximately 5 mm to approximately 50 mm; approximately 5 mm to approximately 25 mm; approximately 5 mm to approximately 15 mm; approximately 10 mm to approximately 20 mm; approximately 20 mm to approximately 30 mm; approximately 30 mm to approximately 40 mm; approximately 40 mm to approximately 50 mm; approximately 50 mm to approximately 60 mm; and approximately 60 mm to approximately 70 mm.

Each flow channel may have a length of approximately 10 mm to approximately 100 mm in length; approximately 20 mm to approximately 100 mm; approximately 30 mm to approximately 100 mm in length; approximately 40 mm to approximately 100 mm in length; approximately 50 mm to approximately 100 mm in length; approximately 60 mm to approximately 100 mm; approximately 70 mm to approximately 100 mm; approximately 80 mm to approximately 100 mm; approximately 90 mm to approximately 100 mm; approximately 10 mm to approximately 50 mm; approximately 10 mm to approximately 40 mm; approximately 10 mm to approximately 30 mm; approximately 10 mm to approximately 20 mm; approximately 50 mm to approximately 100 mm; approximately 50 mm to approximately 90 mm; approximately 50 mm to approximately 80 mm; approximately 50 mm to approximately 70 mm; approximately 50 mm to approximately 60 mm.

Each flow channel may have a depth or height of approximately 100 µm to approximately 500 µm; approximately 100 µm to 400 µm; approximately 100 µm to approximately 300 µm; approximately 100 µm to approximately 200 µm; approximately 200 µm to approximately 300 µm; approximately 300 µM to approximately 400 µm; approximately 400 µm to approximately 500 µm.

In various embodiments, the length, depth or height of the flow channels may be optimized for the type of material being assayed. For example, larger dimensions may be used when analyzing whole cells or cell populations, whereas smaller dimensions may be used when analyzing acellular fractions or chemical libraries and the like.

Figure 11:
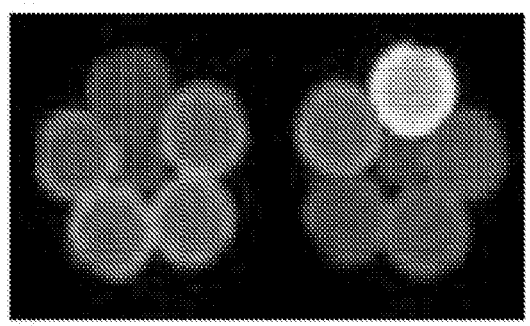
FIG. 11 is a set of images showing an example microwell designed to contain 6 drops, pre-merge (top) and post-merge (bottom).
Figure 11:
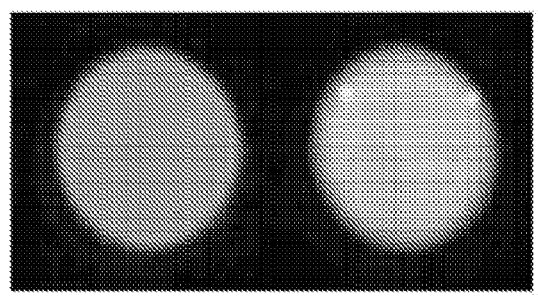
Figure 12:
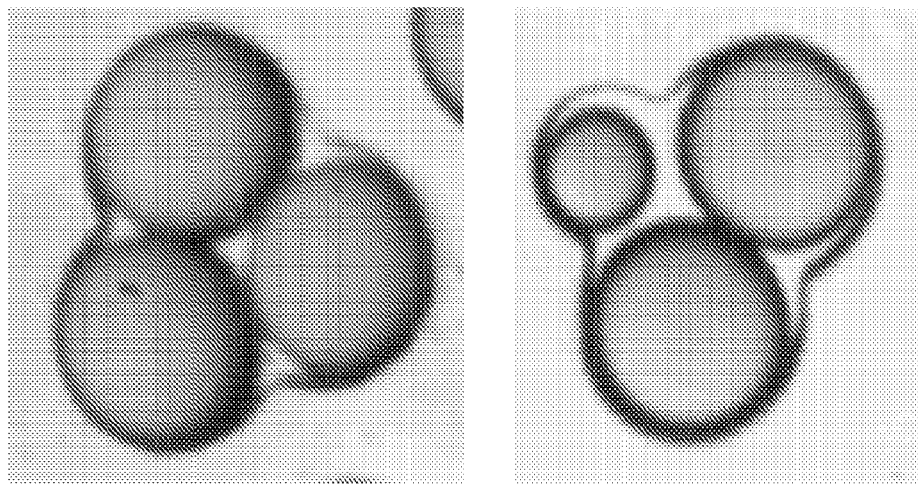
FIG. 12 is a pair of images showing an example microwell with equally sized hemispheres (left) and different sized hemispheres (right), with the different sized hemispheres allowing for the capture and merging of droplets of different sizes.
Figure 13:
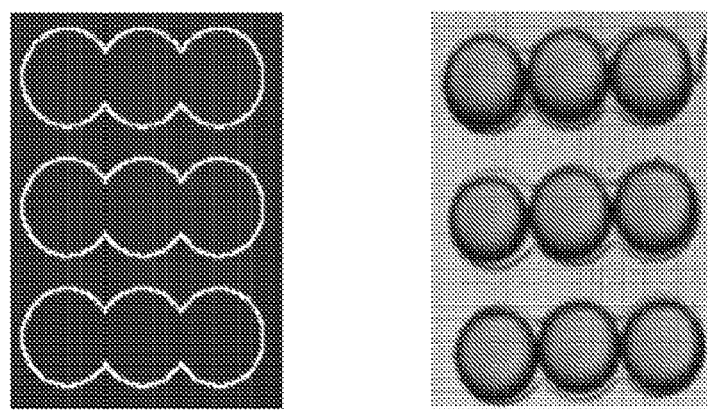
FIG. 13 is a schematic (left) and image (right) of an example microwell design comprised of three equally sized and linearly arranged hemispheres.
Figure 14:
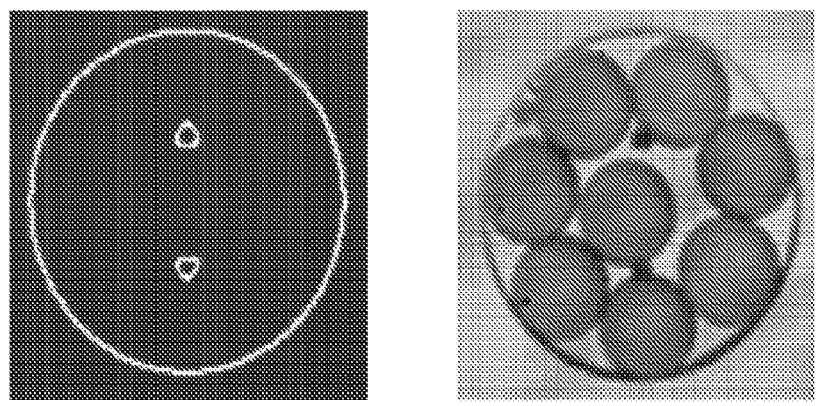
FIG. 14 is a schematic (left) and image (right) of an example microwell design comprising a single circular microwell sized to hold eight droplets.
Figure 15:
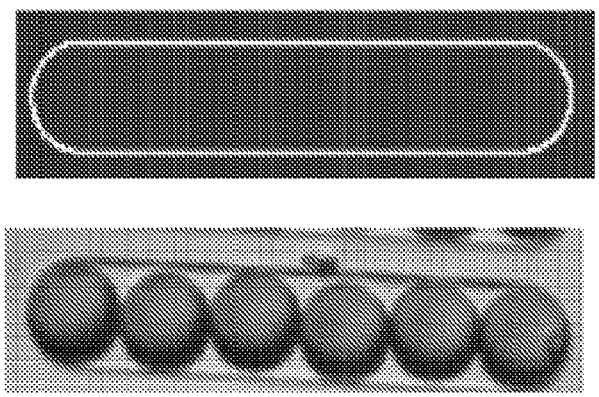
FIG. 15 is a schematic (top) and image (bottom) of an example microwell design comprising a single linear shaped microwell sized to hold six droplets.
Figure 16:
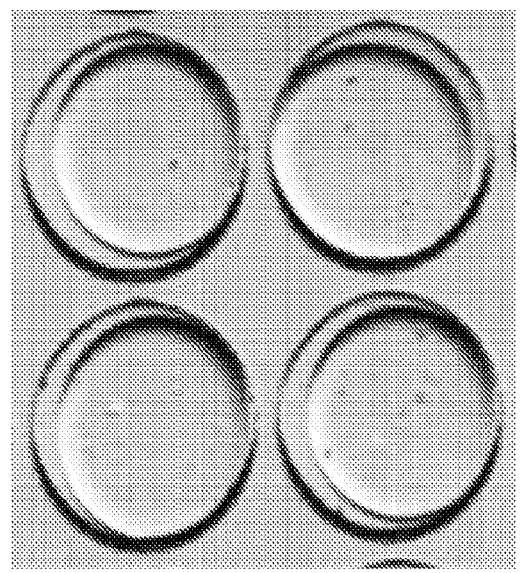
FIG. 16 is an image of example microwells sized to hold single droplets.

The flow channels allow flow beneath a top layer 210 of the microfluidic device comprising an array of microwells 215. In alternative embodiments the flow channels may allow flow of a carrier fluid above a bottom layer of the microfluidic device comprising an array of microwells. Such an embodiment would be an inverted version of the embodiment shown in FIG. 2. The microwells are sized to hold a particular number of individual drops which will then be merged into a single droplet allowing the contents of the individual drops to combine. For example, the wells may be sized to hold two, three, four, five, six, seven, eight, nine, or ten individual drops. The microwells may comprise different shapes and sizes. In certain example embodiments, the microwell may comprise two, three, four, five or six joined hemispheres. The hemisphere may be joined linearly (See FIG. 13) or radially (See FIG. 11). In another example embodiment, the microwells may comprise a circle, oval, or any other shaped appropriately sized to hold the desired number of individual droplets. In certain example embodiments, microwells may further comprise spacers to assist in ordering the droplets within the microwell (See FIG. 14). The maximum number of droplets per microwell is dictated by the stability of the resulting merged droplet. Droplets may range from 10 pL to 10 nL in size.

The array of microwells 215 is located in a layer above or below the flow channel 205 and is situated such that each microwell in the array is accessible via the flow channel 205. In certain example embodiments, there is a single array of microwells 215 located above a single flow channel 205. In certain other example embodiments, there may be two or more arrays of microwells, each situated above a separate flow channel. In certain example embodiments, the number of microwells may range from 1,000 to 1,000,000.

In certain example embodiments, the microfluidic device may further comprise one or more droplet outputs for collecting the merged droplets off the device for further downstream processing. In certain example embodiments, to elute the merged droplets, the device is inverted and the merged droplets are allowed to enter the flow channel which then directs flows of the released merged droplets to the one or more droplet outputs.

Figure 3:
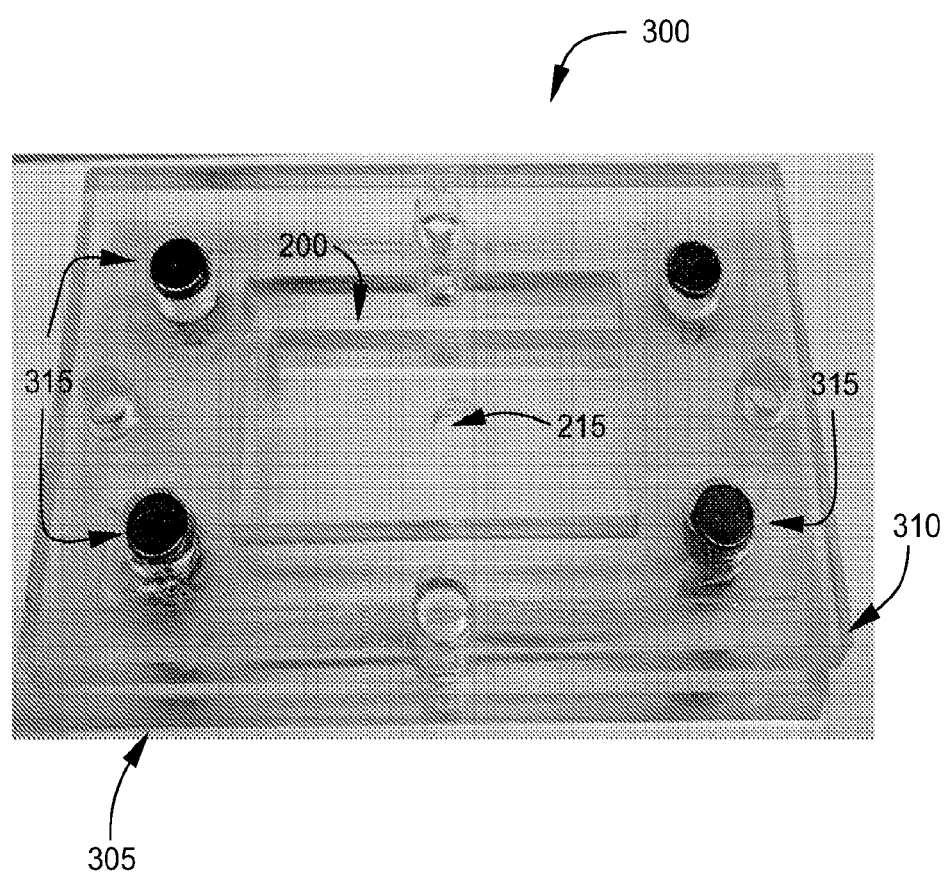
FIG. 3 is an image depicting a clamping mechanism for use in loading a microfluidic device, in accordance with certain example embodiments.
Figure 4:
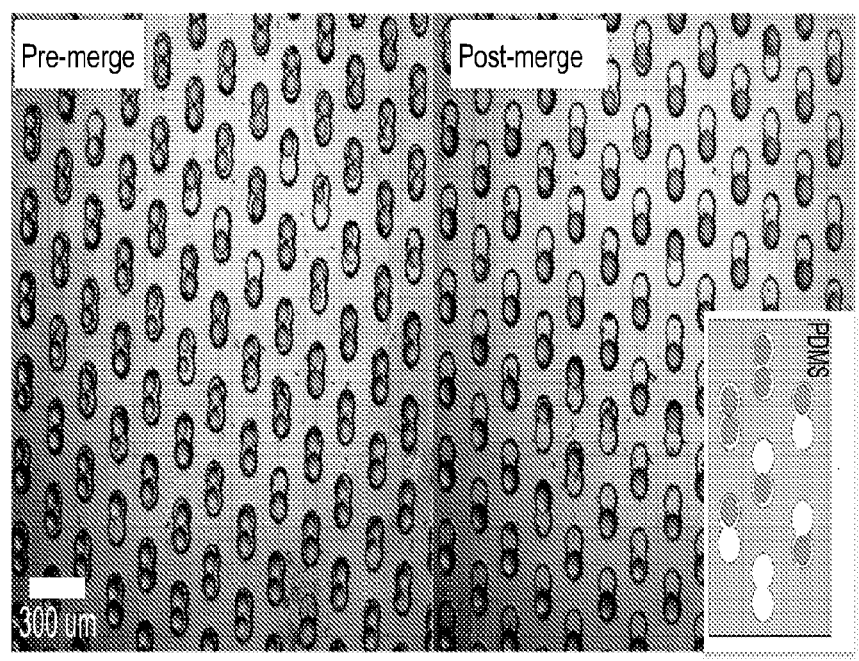
FIG. 4 is an image demonstrating merging of droplets in the microwell array via an applied electric field, in accordance with certain example embodiments. The left panel shows the droplets after loading and sealing of the device with a magnetic clamp. The right panel shows the resulting merged droplets after application of an electric field to the device.

In certain example embodiments, the microfluidic device may further comprise a clamping mechanism for loading the device. Referring to FIG. 3, and in accordance with certain example embodiments, the clamping mechanism 300 may comprise a bottom clamp 305 and a top clamp 310. The bottom clamp 305 may further comprise a glass slide (not shown) onto which the microfluidic device 200 is placed. The bottom clamp may also further comprise one or more spacers (not shown) that define the flow channel beneath the array of microwells when inserted between the glass slide and the microfluidic device 215. When removed the spacers allow the top 310 and bottom 305 clamps to seal the microfluidic device against the glass slide of the bottom clamp 305. The top clamp 310 may comprise an opening sized to fit the microfluidic device such that a portion of the microfluidic device 200 sits above the opening in the top clamp 310. The top clamp 310 and bottom clamp 305 are clamped together by one or more connectors 315. In certain example embodiments, the connections may be one or more magnets, such as but not limited to, rare earth magnets. In certain example embodiments the top 310 and bottom 305 clamps are made from acrylic or other similar material.

Figure 17:
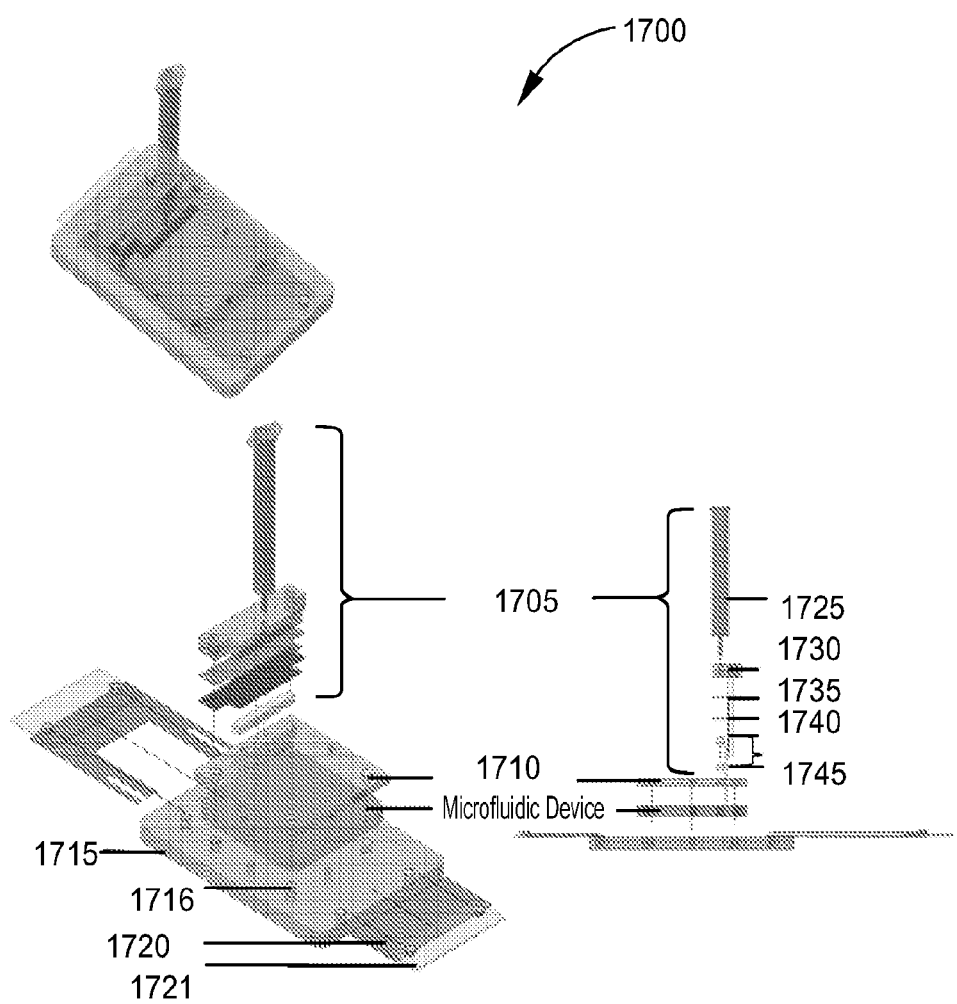
FIG. 17 is a schematic of an example loading system for use with microfluidic devices disclosed herein.
Figure 18:
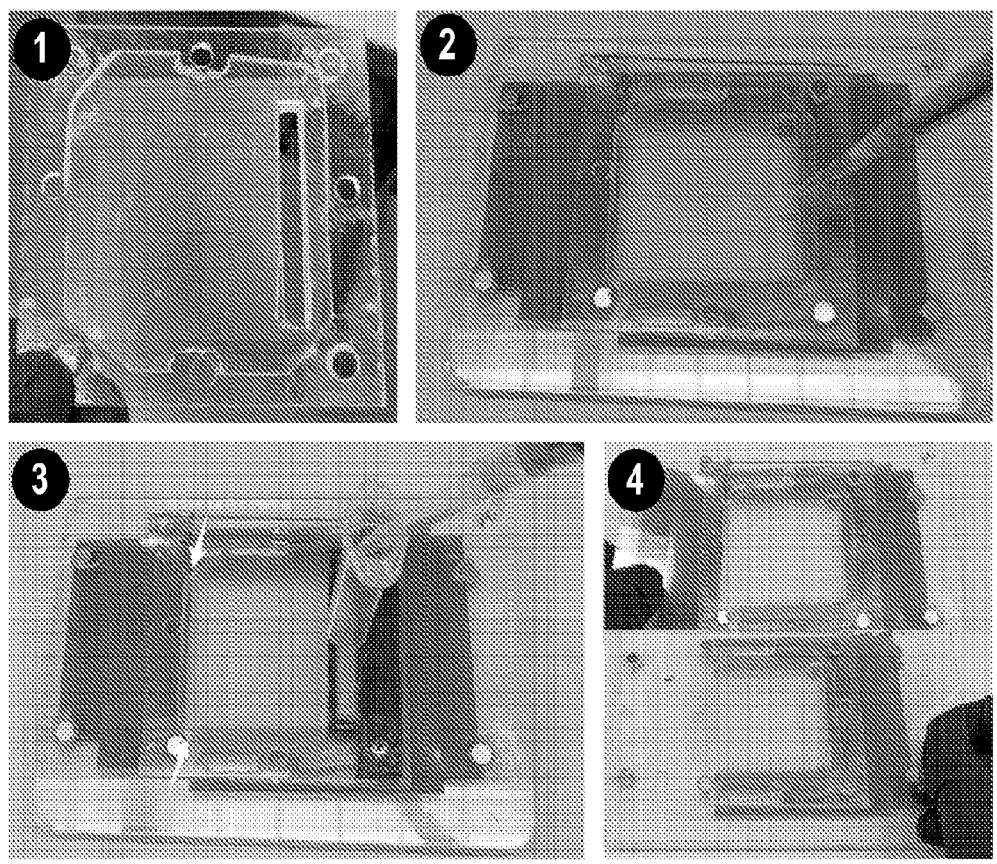
FIG. 18 is a series of photographs demonstrating an example loading procedure for loading droplets and carrier oil onto microfluidic devices disclosed herein. (1) The microfluidic device is aligned on a clamp. (2) The microfluidic device is clamped to the stage with spacers in between the stage and chip. Droplets are loaded by pipette. (3) The loading device is used to flow oil through the microfluidic device, spreading the droplets among the microwells. (4) The spacers are removed.
Figure 19:
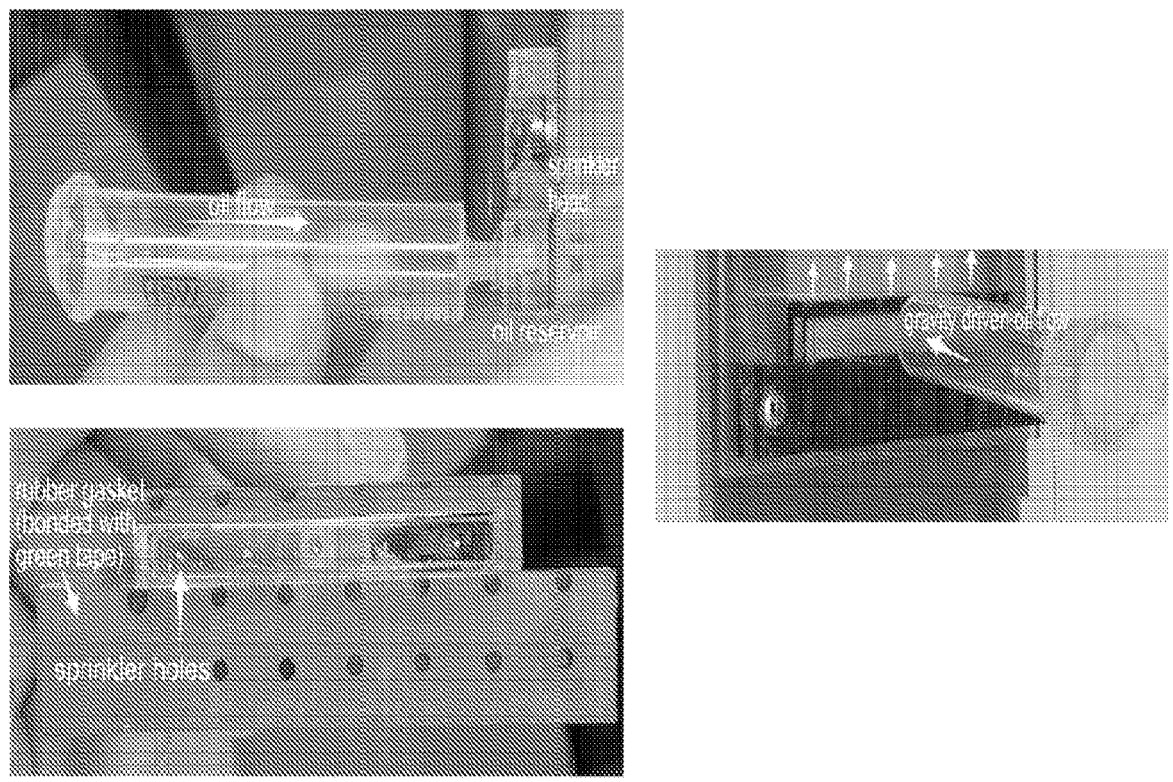
FIG. 19 is a series of photographs showing different views of an example "sprinkler" loading element for use in the loading systems described herein.

In certain example embodiments, the microfluidic device may be loaded using a loading system 1700. Referring to FIG. 17, an example system may comprise a loading device 1705, a clamp 1710, a base 1715, and spacers 1720. The loading device 1705 may comprise an oil reservoir 1725, and adapter 1730, an optional adhesive layer 1735, an optional gasket 1740, and a flow channel interface 1745. The microfluidic device may be placed on the base 1715 and secured to the base with clamp 1710. In certain example embodiments, the clamp 1710 may be secured to the base 1715 via one or more magnets 1716 in the clamp positioned to align with one or more corresponding magnets in the base 1715. The clamp 1710 may have an opening or cut out to allow the loading device 1705 to be aligned with an inlet for loading droplets and carrier oil onto a microfluidic device. Spacers 1720 may be inserted between the base 1715 and the microfluidic device to define one or more flow channels under the array of microwells on the microfluidic device. After loading of droplets into the microwells on the microfluidic device, the spacers may be removed to allow the clamp 1710 to completely seal the microfluidic device against the base 1715. The spacers 1720 may further comprise handles 1721 to facilitate insertion and removal of the spacers from the system. The adapter 1730 facilitates connection of the oil reservoir to the flow channel interface 1745. The adhesive layer 1735 and a gasket 1740 may be used to secure the oil reservoir 1725 and adapter 1730 to the flow channel interface. The flow channel interface 1745 is sized to properly connect with an inlet on the microfluidic device. In one example embodiment, the flow channel interface is rectangular in shape and sized to fit a correspondingly sized and shaped inlet on the microfluidic device. The flow channel interface 1745 may further comprise a series of regular space holes ("sprinkler hole" to facilitate dispersion of a carrier oil into a flow channel running beneath the array of microwells on the microfluidic device.

Microfluidic devices disclosed herein may be silicone-based chips and may be fabricated using a variety of techniques, including, but not limited to, hot embossing, molding of elastomers, injection molding, LIGA, soft lithography, silicon fabrication and related thin film processing techniques. Suitable materials for fabricating the microfluidic devices include, but are not limited to, cyclic olefin copolymer (COC), polycarbonate, poly(dimethylsiloxane) (PDMS), and poly(methylacrylate) (PMMA). In one embodiment, soft lithography in PDMS may be used to prepare the microfluidic devices. For example, a mold may be made using photolithography which defines the location of the one or more flow channels and the array of microwells. The substrate material is poured into a mold and allowed to set to create a stamp. The stamp is then sealed to a solid support such as, but not limited to, glass.

Due to the hydrophobic nature of some polymers, such as PDMS, which absorbs some proteins and may inhibit certain biological processes, a passivating agent may be necessary (Schoffner et al. Nucleic Acids Research, 1996, 24:375-379). Suitable passivating agents are known in the art and include, but are not limited to, silanes, parylene, n-Dodecyl-b-D-maltoside (DDM), pluronic, Tween-20, other similar surfactants, polyethylene glycol (PEG), albumin, collagen, and other similar proteins and peptides.

The microfluidic devices may further comprise inlet and outlet ports, or openings, which in turn may be connected to valves, tubes, channels, chambers, and syringes and/or pumps for the introduction and extraction of fluids into and from the microfluidic device. The microfluidic devices may be connected to fluid flow actuators that allow directional movement of fluids within the microfluidic device. Example actuators include, but are not limited to, e.g., syringe pumps, mechanically actuated recirculating pumps, electroosmotic pumps, bulbs, bellows, diaphragms, or bubbles intended to force movement of fluids.

Methods for Combinatorial Screening

In certain aspects, the embodiments disclosed herein are directed to methods of combinatorial screening of molecular species. The methods may be used to combine and screen any pre-defined molecular species at any pre-defined concentrations. As used herein, a molecular species refers to both a chemically distinct molecule, or the same molecule at different concentrations. For example, a first library comprising a first set of chemically distinct molecular species may be defined, and a second library comprising a second set of chemically distinct molecular species for combining with the first set of species may be defined. Alternatively, the same chemical species may be prepared at a range of different concentrations. The molecular species may be screened in the presence of one or more cells. The molecular species may be further screened in the presence of a reporter construct to measure the combinatorial effect of the combined species. By way of example only, a set of antibiotics may be screened in combination with a set of different adjuvants over a range of different antibiotic and adjuvant combinations and in replicates. Other combinatorial screens may be done. For example, the methods may be used to screen a library of drug candidates. The methods may also be used to screen the effect of a set of genetic perturbations on a cell.

Figure 1:
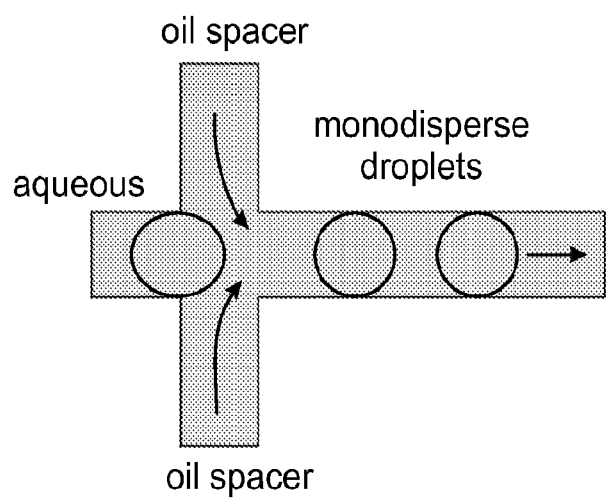
FIG. 1 is a diagram depicting a microfluidic device used for droplet production, in accordance with certain example embodiments.

Each molecular species to be tested (distinct molecule or concentration) may be placed in a microplate well. For example, a 94 or 384 microplate well. Droplets comprising the molecular species from the wells are then formed using standard droplet formation procedures. For example, a device comprising an aqueous input channel and one or more oil input channels may be used to form mono-disperse droplets. See FIG. 1. The aqueous input channel is fed with an aqueous solution comprising the species to be screened. The aqueous solution is then combined with an oil solution flowing from the one or more oil input channels to generate mono-disperse droplets comprising the species to be screened. The droplets may be formed off chip and then loaded via the droplet input onto the microfluidic device. Alternatively, the microfluidic device 200 may be connected directly to a second microfluidic device for forming droplets which then feeds the formed droplets on the microfluidic devices 200 via a droplet input.

To track and identify each molecular species and resulting combination of species, each molecular species is labeled, e.g., with a barcode. For example, a barcode may be added to each well with a distinct molecular species. Accordingly, when droplets are formed, the barcode is incorporated into the droplet along with the molecular species. Thus, each droplet carrying a molecular species will also carry a unique barcode, and when two or more droplets are merged, the combined molecular barcodes will identify which molecular species are present in the merged droplet.

Figure 5:
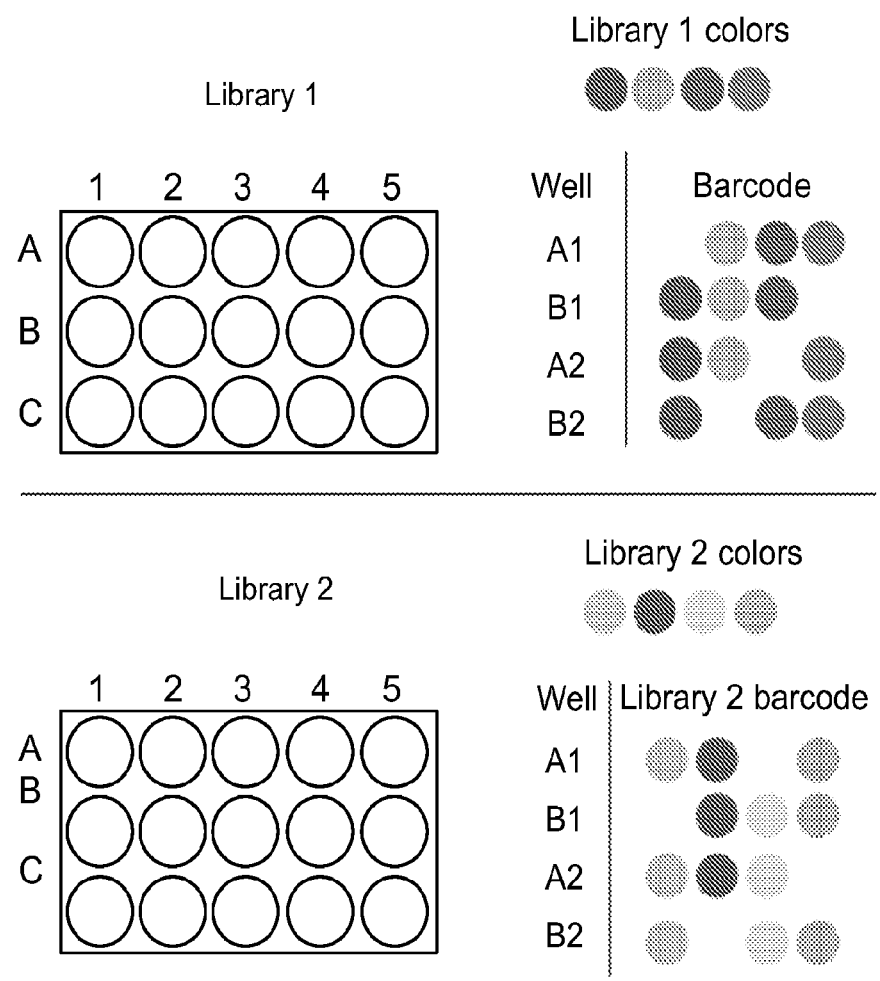
FIG. 5 is a diagram depicting an optical barcoding scheme, in accordance with certain example embodiments. Each molecular species in a library is assigned a subset of fluorescent beads of distinguishable colors.
Figure 6:
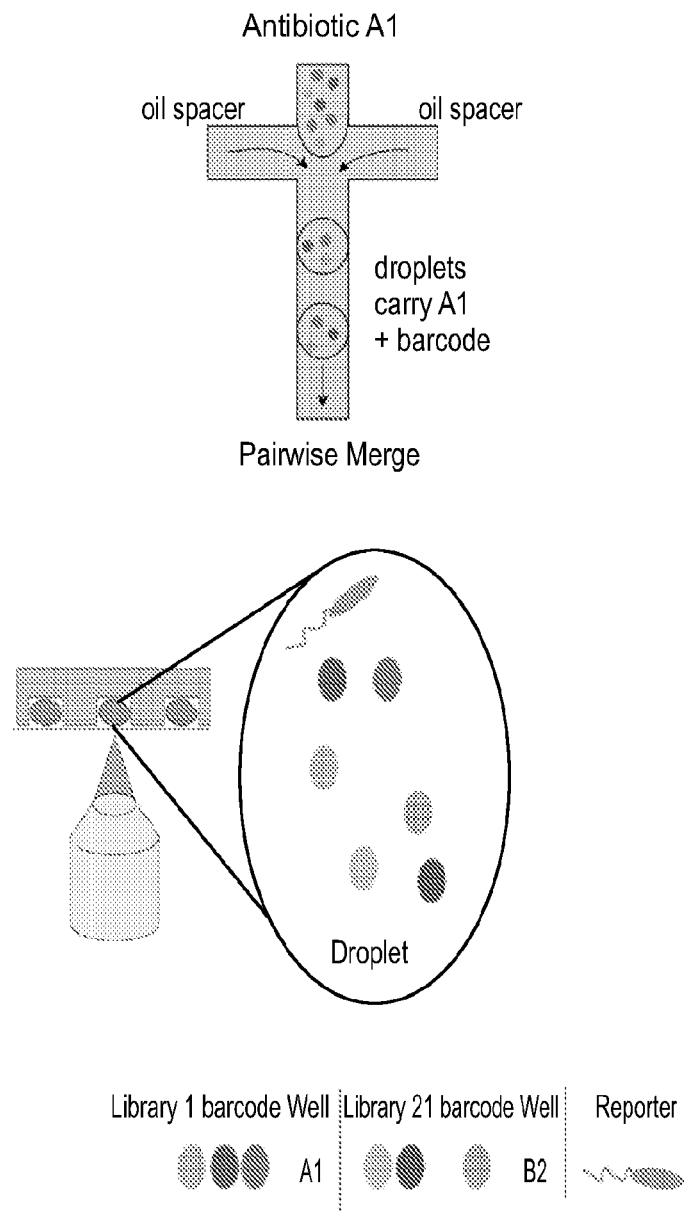
FIG. 6 is a diagram depicting a procedure for using the optical barcoding scheme, in accordance with certain example embodiments. Droplets are formed by mixing antibiotic A1 with oil in a pairwise merge with optional barcode. Droplets carrying molecular species are mixed with the corresponding subsets of fluorescent beads, and a first population of mixed droplets are created. After mixing with a second population of droplets carrying molecular species from a second library, the microwell array randomly merges droplet pairs. Fluorescence imaging of the droplets then indicates the subset of fluorescent beads, and thus the agent in the merged droplet is identified. At the same time, a reporter is measured to provide a readout of the activity being screened.
Figure 8:
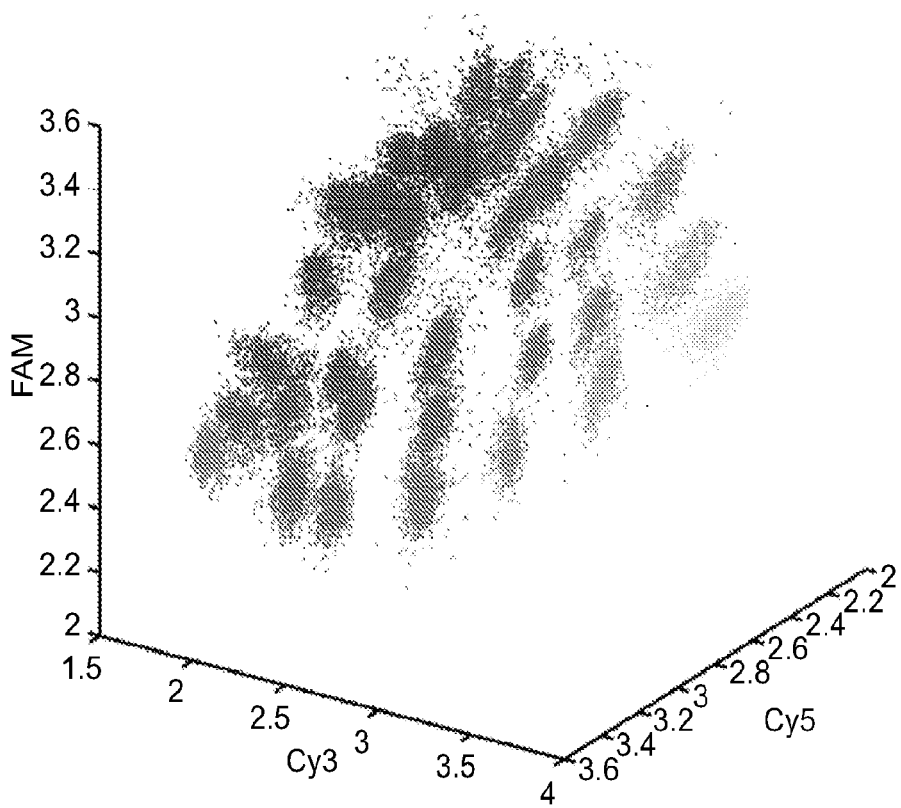
FIG. 8 is (A) a graph depicting 37 distinguishable colors produced by varying the ratios of just three colors, in accordance with certain example embodiments. The three axes show blue, green, and red fluorescence, and each point shows a different bead imaged with a fluorescence microscope. (B) Is a graph depicting the number of unique barcodes that may be generated from the barcoding scheme, in accordance with certain example embodiments. The scaling is shown for barcodes composed of subsets of three, four, and five colors. Using subsets of four colors, nine distinguishable colors are sufficient to uniquely barcode 96 molecular species, and 11 colors are sufficient to uniquely barcode 384 molecular species.
Figure 8:
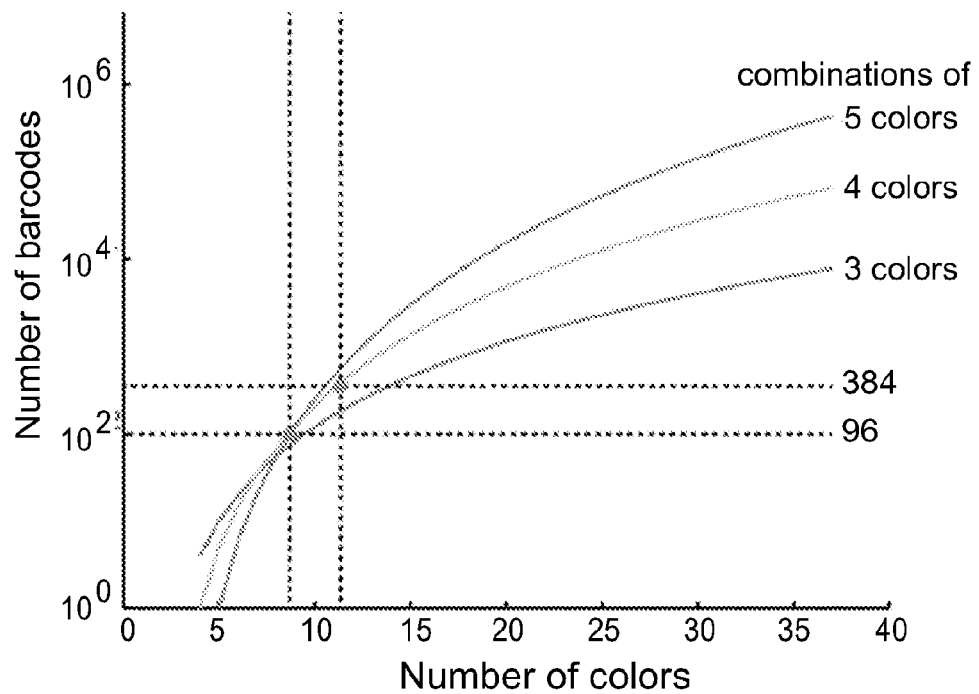
Figure 9:
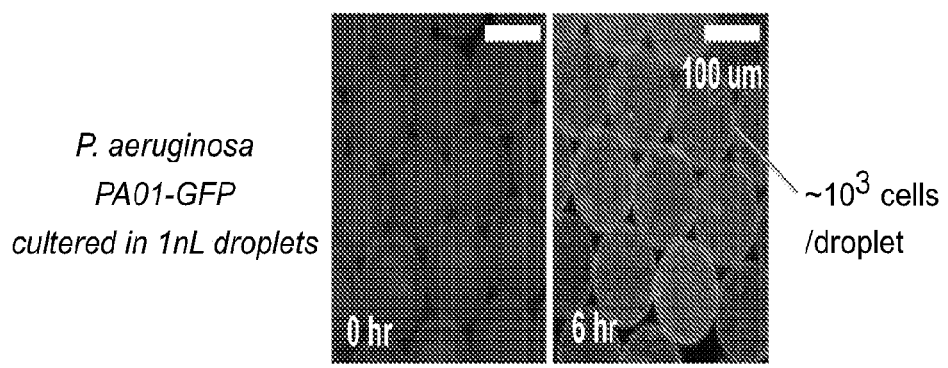
FIG. 9 is an image depicting detection of a reporter, the growth of *Pseudomonas aeruginosa* expressing green fluorescent protein (GFP). The cells are loaded into droplets and imaged via fluorescence microscopy.
Figure 10:
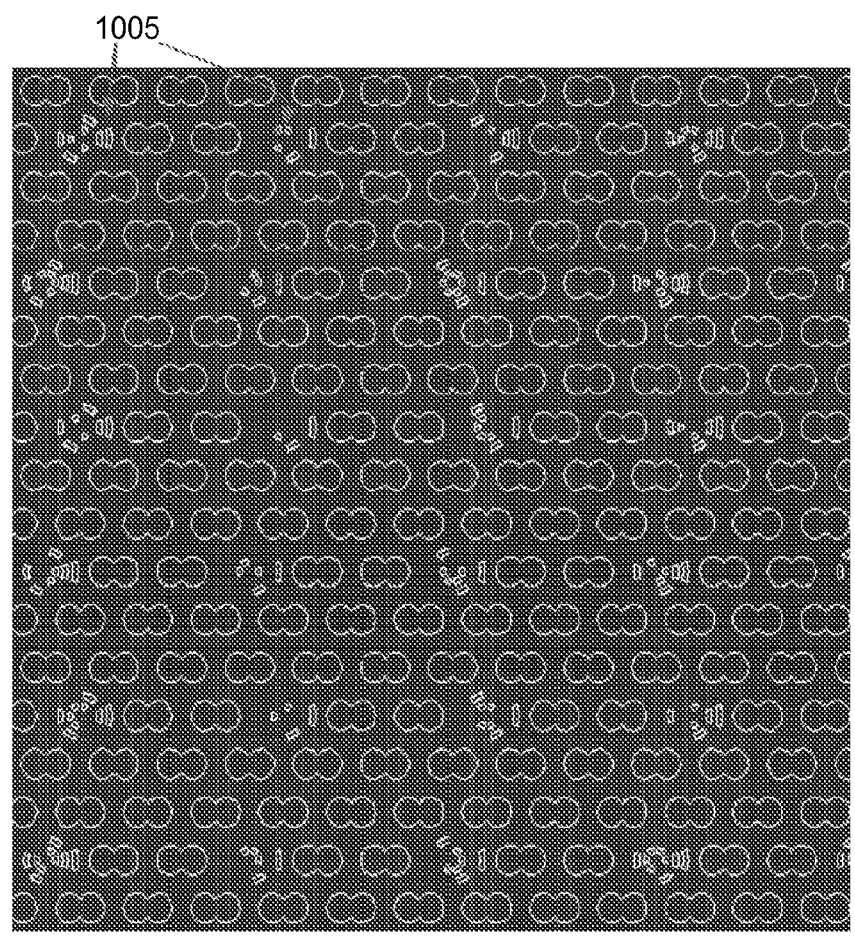
FIG. 10 is a diagram showing a CAD design of a microfluidic device in accordance with certain example embodiments. The microwells are 150 μm diameter and are shaped to allow selective incorporation of two 1 nL droplets. Unique topographical features (1005) may be incorporated at certain locations on the device to retain spatial information when imaging.

The barcode may be an optically detectable barcode that can be visualized with light or fluorescence microscopy. In certain example embodiments, the optical barcode comprises a sub-set of fluorophores or quantum dots of distinguishable colors from a set of defined colors. See, for example, FIG. 5 where each well of an example library 1 and library 2 receive a unique combination of optically detectable labels. As shown in FIG. 8A, a total of 37 distinct colors may be generated by varying the ratio of only three dyes. An expanded palette may be created, for example by varying the ratio of more than three dyes. However, only 18 distinct colors are needed to barcode screens of 96×96 molecular species (9 per library), and only 22 colors are needed to barcode screens of 384×384 molecular species (11 per library). FIG. 8B show the possible number of unique barcodes that may be achieved by varying the ratios of three colors, four colors, and five colors and the upward scalability of the methods disclosed herein. In certain example embodiments, beads are labeled with the different ratios of dyes to form the set of defined colors from which the optical barcodes may be derived. For example, the beads may be polystyrene beads labeled with biotin conjugated dyes. Alternatively, the optical barcodes may be derived using combinations of optically detectable objects. For example, an optical barcode can be defined from a set of objects, such as beads, that vary in size, shape, color, or a combination thereof.

In certain example embodiments, barcodes comprise a unique oligonucleotide sequence. An oligonucleotide barcode is generated by sequentially attaching two or more detectable oligonucleotide tags to each other. As used herein, a "detectable oligonucleotide" tag is an oligonucleotide that can be detected by sequencing of its nucleotide sequence and/or by hybridization to detectable moieties such as fluorescently labeled probes. The oligonucleotide tags that make up a barcode are typically randomly selected from a diverse set of oligonucleotide tags. For example, an oligonucleotide tag may be selected from a set A, B, C, and D, each set comprising random sequences of a particular size. An oligonucleotide tag is first selected from set A, then a second oligonucleotide tag is selected from set B and concatenated to the oligonucleotide from set A. The process is repeated for sets C and D. The particular sequence selected from each set and the order in which the oligonucleotides are concatenated define a unique barcode. Methods for generating barcodes for use in the constructs disclosed herein are described, for example, in International Patent Application Publication No. WO/2014/047561. The oligonucleotide barcodes may be incorporated into the droplets by attaching the oligonucleotide barcodes to beads, similar to those used with the optical barcodes, and loading the oligonucleotide labeled beads into the wells of each molecular sample. Oligonucleotide barcodes may also be detected off-chip as described in further detail below.

In certain example embodiments, the droplets may further comprise one or more cells. For example, one or more bacteria against which an antibiotic to be screened is targeted may be loaded into one set of droplets and then later merged with a droplet comprising one of the antibiotic compounds to be screened. The cell may function as a reporter system for growth, metabolic growth, and/or as a stress sensor. For example, the cell may generate a detectable sequence when a certain desired effect by the combined molecular species is achieved. Other cell types, including eukaryotic cells, and reporter systems may also be used depending on the type of screen being conducted. For example, certain anti-cancer therapeutics may be screened in the presence of target cancer cell lines. With embodiments that involve the culture of certain cell types, the droplets will be formed from an aqueous solution comprising the appropriate growth media. In certain example embodiments, the reporter cells may function as a reporter by direct observation of morphological changes in the cells. In certain other example embodiments, the cells may be designed to express an optically detectable marker. For example, cells may express a fluorescent protein as a marker of metabolic activity. Decreases in fluorescence may indicate reduced viability in the presence of certain molecular species being screened.

In certain example embodiments, the reporter may comprise a detection agent capable of detecting an agent in the merged droplet. For example, the agent may be a reactant resulting from the combination of the two molecular species, or a particular cellular compound generated by a cell when exposed to the particular combination of molecular species in a droplet. In certain example embodiments, the detection agent may comprise an optically labeled antibody or nucleic acid.

Once the barcoded droplets comprising the various molecular species to be merged are formed, the droplets are loaded into the droplet input of the microfluidic devices disclosed herein. In certain example embodiments, a carrier oil is first loaded through the droplet input 215 until the device 200 is primed. Suitable carrier oils include fluorocarbon oils. The droplets are then loaded via the droplet input and into the one or more flow channels 205. As the droplets are carried by the oil through the flow channel 205 underneath or above the array of microwells 215, the buoyancy either lifts or drops the droplets into vacant microwells until the microwells are filled. The droplets are randomly distributed throughout the microwells. The droplets in carrier oil may be distributed through the one or more flow channels 205 and into the microwells 215 by a pumping mechanism. Alternatively, the droplets may be distributed by gently rocking the microfluidic device 200 for period of time sufficient to load most if not all microwells with droplets.

A certain percentage of microwells may contain two droplets carrying the same molecular species. These wells may function as built-in controls. However, the scale at which the droplets combined helps ensure an adequate representation of all possible combinations between different species. In certain example embodiments, the number of microwells imaged is approximately 15 times the number of droplets to be generated. Additional, carrier oil may be flushed through the system to remove any droplets that did not load into a microwell.

After the droplets have been loaded into the microwells, the droplets are merged in parallel. The droplets may be merged by any mechanism sufficient to coalesce two or more droplets into a single droplet, such as but not limited to, electrocoalescence, thermal coalescence, acoustic coalescence, vortexing, or changes in surfactant concentration. In certain example embodiments, the droplets are merged using electrocoalescence. For example, a suitable electric field may be applied to the microfluidic device using a corona treater wand. In certain other example embodiments, coalescence can be triggered by surfactant depletion. For example, the inside of the microwells may be modified with surface treatment chemistry that binds surfactant thereby depleting surfactant available to the droplets. Alternatively, a solution may be flushed through the system that washes surfactant out of the microwells. Standard droplet coalescence methods that may be used with the embodiments described herein are described in Niu et al. "Electro-Coalescence of Digitally Controlled Droplets," Analytical Techniques (2009) 81(17), 7321-7325; Niu et al. "Pillar-induced droplet merging in microfluidic cirucits" Lab On A Chip (2008), 8(11), 1837-1841; and Mazutis et al. "Selective droplet coalescence using microfluidic systems," (2012), Lab on a Chip, 12, 1800-1806.

Figure 7:
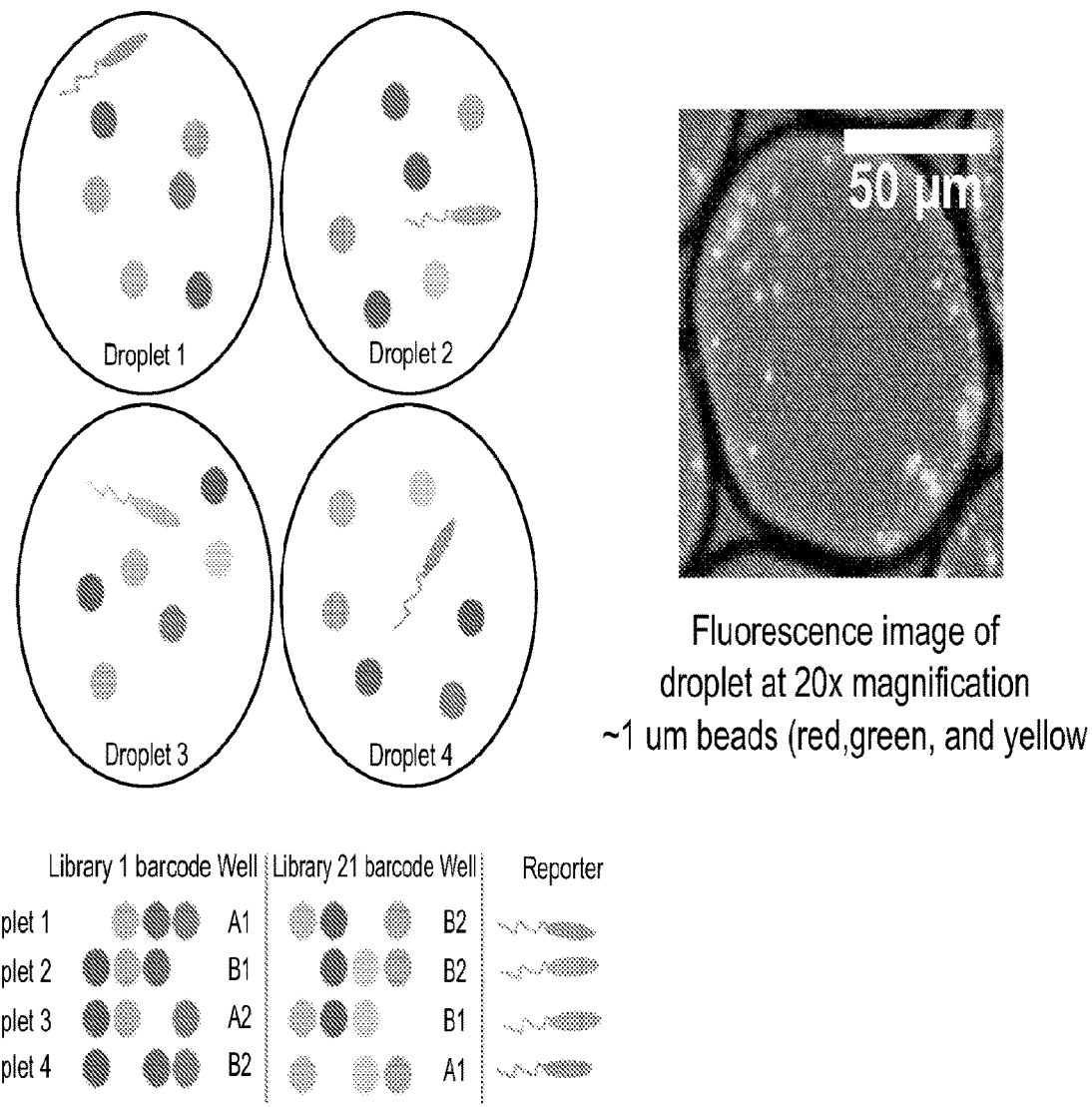
FIG. 7 is a diagram depicting the parallel imaging of droplets and corresponding identification of the molecular species carried in the droplets and simultaneous measurement of a reporter, in accordance with certain example embodiments. The right panel shows a fluorescence micrograph of a droplet carrying three distinguishable colors of fluorescent beads.

After the droplets are merged, the identity of molecular species in each well is determined by optically scanning each microwell to read the optical barcode and measure the reporter when present. The embodiments disclosed herein are compatible with standard high content imaging microscopes for rapid imaging. In certain example embodiments, only low magnification (20×) is required. As shown in FIG. 7, the unique optical barcode of each well can be observed and related back to the associated molecular species. Further, the level of reporter may be observed. Optically barcoding droplets with a reporter system allows for simultaneous optical phenotyping and molecular species identification.

Depending on the reporter system used and the molecular species being screened, the microfluidic device 200 may be incubated for a period of time prior to imaging. In addition, the microfluidic device 200 may be imaged at multiple time points to track changes in the measured amount of reporter over time. In certain example embodiments, further perturbations may be made to the system after the droplets are merged and prior to imaging the microwells. A common agent may be delivered to all merged droplets in each microwell. For example, where cells are being cultured in the droplets, the growth media inside the droplet may be replenished by flowing the appropriate culture media through the one or more flow channels 205 of the device 200. Alternatively, the combinatorial screen may be designed to take place in the presence of an expressed protein under the control of an inducible promoter. The promoter for inducing expression may be delivered to the cells by flowing a solution comprising the promoter through the flow channel 205 to allow for diffusion of the promoter into the merged droplets. Any common agents that may be needed to effectuate the screen may be delivered to all merged droplets in this fashion.

Droplets may leak contents over time. Compound leakage is surfactant mediated. For example, excess surfactant can form small bubbles off of existing droplets and in the process carry off droplet contents when the small bubbles release from the main droplet. Therefore, in certain example embodiments, the merged droplets may be washed with a reagent to bind free surfactant and/or reduce the surfactant concentration to the lowest possible concentration required for forming droplets. In certain example embodiments, the reagent used to wash out excess surfactant is perfluorooctanol. Other similar fluorinated oils and reagents capable of solvating the surfactant may be used as well. In certain example embodiments, the surfactant concentration is reduced to approximately 0.3% w/w. Alternatively, the microfluidic device may be sealed such that maintaining droplet formation is no longer required. For example, where the clamp device and spacers are used as described above, removal of the spacers removes the flow channel sealing the microwells against the glass slide and thereby preventing redistribution of microwell contents.

In certain embodiments, the methods disclosed herein may further comprise eluting the merged droplets off of the microfluidic device 200 for downstream processing applications. In one example embodiment, the merged droplets may be eluted off the device 200 by inverting the device 200 and loading a carrier oil into the one or more flow channels. The buoyance of the droplets will cause the merged droplets to rise out of the microwells and into the flow channel 205, wherein the merged droplet may be eluted with the carrier oil as it is drained or pumped out of the microfluidic device 200.

In certain example embodiments, each well comprising a molecular species to be screened receives a unique label, such as but not limited to, a unique oligonucleotide barcode, which identifies the molecular species. The unique label should be able to hybridize or bind to another unique label associated with another molecular species. Accordingly, when droplets comprising the molecular species are formed, the unique label is incorporated into the droplet with the molecular species. The droplets are loaded onto the microfluidic device 200 and merged as described above. The droplets are eluted from the device. The microwells may or may not be imaged on the device prior to elution of the droplets from the device. In certain example embodiments, the droplets are sorted. For example, at least one set of droplets may further comprise a reporter molecule that indicates the presence of a desired activity in the droplet. The reporter may or may not be optically detectable. In certain example embodiments, the reporter produces a fluorescent signal and the merged droplets are sorted, for example, using flow cytometry. Those droplets with the detected desired activity are then ruptured and the unique label which identifies each molecular species present in a merged droplet is identified. In certain example embodiments, the unique label is an oligonucleotide barcode. The oligonucleotide barcode may have "sticky ends" that allows any two oligonucleotide barcodes to at least partially hybridize to each other. When two individual droplets are merged into a single droplet, the oligonucleotide barcodes for each molecular species hybridize via the sticky ends to form a duplex. The duplex is isolated when the merged droplets are ruptured and the duplex is then sequenced using standard sequencing procedures known in the art. In certain example embodiments, the duplex is first amplified prior to sequence. The amplification may be done after the duplex is isolated from the merged droplets, or it may be done on the device. For example, primers and amplification reagents for amplifying the oligonucleotide barcode may be spiked into the wells for each molecular species prior to loading droplets onto the microfluidic device. Alternatively, the primers and amplification reagents may be delivered to all the merged droplets as described herein. The oligonucleotide barcode information in the sequencing read identifies the two molecular species that were paired in the merged droplet. Other methods for tracking the identify of molecular species may be used, such as those used in Castellarnau et al. Small. 2015; 11(4): 489-498.

In addition to using sequenced barcode information to identify co-localization of molecular species to the same merged droplet, off-chip optical detection of the barcodes may also be used. A set of probes may be derived with each probe in the set capable of specifically hybridizing to one of the possible oligonucleotide tags at each position in the barcode. Each probe for a given oligonucleotide tag may be labeled with a different optically detectable label. In one example embodiment, the optically detectable label is a fluorophore. In another example embodiment, the optically detectable label is a quantum dot. In another example embodiments, the optically detectable label is an object of a particular size, shape, color, or combination thereof. For each position in the barcode, the corresponding set of probes for each possible oligonucleotide tag at that position is allowed to hybridize to the cells. The process is repeated for each position in the barcode. The observed pattern of optically detectable barcodes will be dictated by the order of oligonucleotide tags in the barcode. Accordingly, the barcode may be determined by the optical readout obtained by the sequential hybridization of the probes in the probe set.

In certain example embodiments, the reporter agents may be used to sort the droplets after the droplets are eluted from the microfluidic device and prior to any further downstream applications. For example, where the reporter agent generates a fluorescent signal, flow cytometry may be used to sort droplets with a detectable fluorescent signal from those that do not, thereby allowing the set of droplets requiring further downstream analysis to be reduced on only droplets comprising the desired activity or combination of molecular species to be selected.

Methods for Pairwise Screening of Antibiotics and Adjuvants

In another aspect, embodiments disclosed herein are directed to methods for screening antibiotic-adjuvants. Antibiotic resistance is rising but new antibiotics discoveries are rare. Instead of discovering new compounds, it may also be possible to re-purpose existing drugs by overcoming intrinsic or acquired resistance mechanisms. In addition, it may also be possible to rescue drugs that were too toxic by determining a lower minimal effective dose, or to preemptively combat evolution of resistance by using combinatorial therapy. For example, the use of adjuvants may expand the efficacy of existing drugs. Adjuvants potentiate drug activity by affecting vital bacterial functions such as permeability, efflux pump inhibition, biofilm formation, changes in oxidative stress, or inhibition of antibiotic cleavage and modification mechanisms (e.g. ß-lactamases).

In certain example embodiments, a first library of antibiotics to be screened is defined and loaded into microplate wells. A second library of potential adjuvants to be screened is defined and loaded into separate microplate wells. Each antibiotic and adjuvant may be run at multiple concentrations. In addition, each species of antibiotic and adjuvant may be run in replicate. Each antibiotic and adjuvant species is optically barcoded by adding a pre-determined unique set of optically detectable labels to each well containing the corresponding antibiotic and adjuvant. In certain example embodiments, the optically detectable labels are fluorescently labeled beads of different colors. See FIG. 5. A reporter bacteria is further included in the wells comprising the candidate adjuvants to be screened. In certain example embodiments, the bacteria comprises a nucleic acid construct encoding a reporter agent. The reporter agent may be a used to measure growth, metabolic activity or function as a stress sensor. In certain example embodiments, the reporter comprises a nucleic acid sequence encoding a fluorescent protein.

Each optically encoded antibiotic and adjuvant is then processed to form droplets according to known methods in the art. In the process of forming droplets, the optical barcode unique to each antibiotic and adjuvant to be screened is incorporated into the droplet along with the corresponding antibiotic or adjuvant.

The droplets comprising the barcoded antibiotics and the barcoded adjuvants and reporter cells are then loaded onto the microfluidic device 200 comprising a microwell array 215. In certain example embodiments, the microwells are sized to capture two droplets per microwell. The microfluidic device 200 may first be loaded with a carrier oil until the device is fully primed. The droplets are then loaded in bulk on the microfluidic device 200. The droplets are then randomly distributed to the microwells via the flow channel. The droplets are buoyant and will rise out of the carrier oil stream and into available microwell spaces. In certain example embodiments, the droplets are circulated in the flow channel 205 by pumps until the droplets are sorted into the microwells. In certain other example embodiments, the droplets are circulated in the flow channel 205 by gently rocking the device 200 until the droplets are sorted into the microwells. Additional carrier oil may be loaded onto the microfluidic device to wash off droplets that do not load into a microwell. Accordingly, most microwells will comprise two droplets with the majority comprising one barcoded antibiotic droplet and one barcoded adjuvant/reporter cell droplet. Some microwells will contain two antibiotic droplets or two adjuvant/reporter cell droplets, or a single droplet. These microwells may serve as built-in control wells.

The droplets are then merged as described herein. Each microwell is then optically scanned using a microscope to detect the barcode of the merged droplet and the reporter molecule. The merged droplets may be incubated on-chip for a period of time, depending on the type of antibiotic/adjuvants screened and the reporter system used. As shown in FIG. 7, the unique optical barcode of each well is observed and used to identify the antibiotic and adjuvant combination in each microwell. In addition, microscopy may be used to measure the reporter present in each microwell. The readouts can be assigned to specific pairs of antibiotics and adjuvants and those combinations producing the desired effect identified. For example, the reporter cell may express a fluorescent protein while the reporter cell is metabolically active. The screen may be to identify antibiotics effective at inhibiting the metabolic activity of the reporter cell. Accordingly, those microwells that exhibit decreased reporter fluorescence may be identified as effective at inhibiting the metabolic activity of the target bacteria.

The additional features described herein for optical phenotyping and molecular species screening may also be applied equally to these methods for screening antibiotic and adjuvant pairs.

EXAMPLES

The following protocols were used in preparation and use of the microfluidic devices disclosed herein.
Microbiology
All microbiology is performed via clinical laboratory standards.
Droplet Production
Droplets are produced according to standard protocols using a fluorinated oil carrier phase.
Device Setup
A glass slide is placed on top of the lower clamp. Two spacer coverslips are aligned to have ~2 mm overlap with the glass slide on either side. Finally, the PDMS microwell array is placed on the spacer coverslips, and the top clamp is placed on top. The magnetic force between the clamps should force the PDMS to stably adhere to the spacer coverslips.
Loading Droplets
The spacer coverslips create a broad channel which underlies the microwell array. First, carrier oil is loaded through the center access well until the device is primed. Droplets are then loaded via micropipette into the center access well on the chip. The device is rocked gently until droplets spread uniformly across the microwells. More oil can be loaded as needed to wash away droplets that do not enter microwells. Finally, the spacer coverslips are manually rotated away, and the PDMS smoothly adheres to the glass under the force of the magnetic clamp.
Merging
The droplets are merged using an applied electric field of >10 kV strength and 10 kHz-10 MHz frequency. This can be applied through a corona treater wand (Electro-Technic Products, Model BD-20), and holding the discharge ~0.5 cm above the device, for ~10 s at high output power.
Fabrication
The microwell device is designed using computer-aided design tools (Autodesk Autocad). Each microwell is designed to hold an integer number of droplets; wells should be designed such that the radius is equal to the droplet radius+10 μm. The wells are spaced at greater than 1 droplet radius. Wells can be packed hexagonally in order to increase density. Symbols encoding spatial coordinates can be sparsely incorporated, substituting for a well where needed.

PDMS chips are fabricated according to standard lithography techniques, using mylar transparency masks. To prevent uptake of small molecules into the PDMS, 100 nm parylene is applied via vapor deposition according to standard protocols.

The magnetic clamp is designed using computer aided design tools (Autodesk Autocad) and can be fabricated via 3D printing or laser cutting. Neodymium rare earth magnets are glued into the clamps after fabrication using standard epoxy.

Bead Production for Optical Barcoding
Materials
Streptavidin coated polystyrene beads (Bangs laboratories)
Biotin conjugated Dyes of choice
Protocol
1) Wash beads 2× in Binding & Washing buffer, as recommended by manufacturer
  a) Add equal volume of binding and washing buffer
  b) Vortex for 10 s
  c) Spin down at 10 k×g for 2 minutes
  d) Remove the supernatant, and replace with fresh wash buffer
  e) the second time resuspend to final volume
2) add dye to beads
3) put on rotator for 1 hr at RT
4) Add 0.1% Tween to prevent the beads from sticking to the tube walls
5) Wash in Binding & Washing+0.1% Tween-20 2× following protocol in step (4).
6) Resuspend in final volume in 0.1% Tween-20+Binding & Washing buffer Commercial Alternatives
Luminex
Bangs labs
Invitrogen
Imaging and Analysis The device is mounted on a standard microscopy stage and imaged according to standard batch fluorescence imaging protocols. Microbial growth is determined via the average fluorescence in each microwell. Optical barcodes are classified according to standard image segmentation and classification procedures.

Adjuvant/Antibiotic Screen

Figure 20:
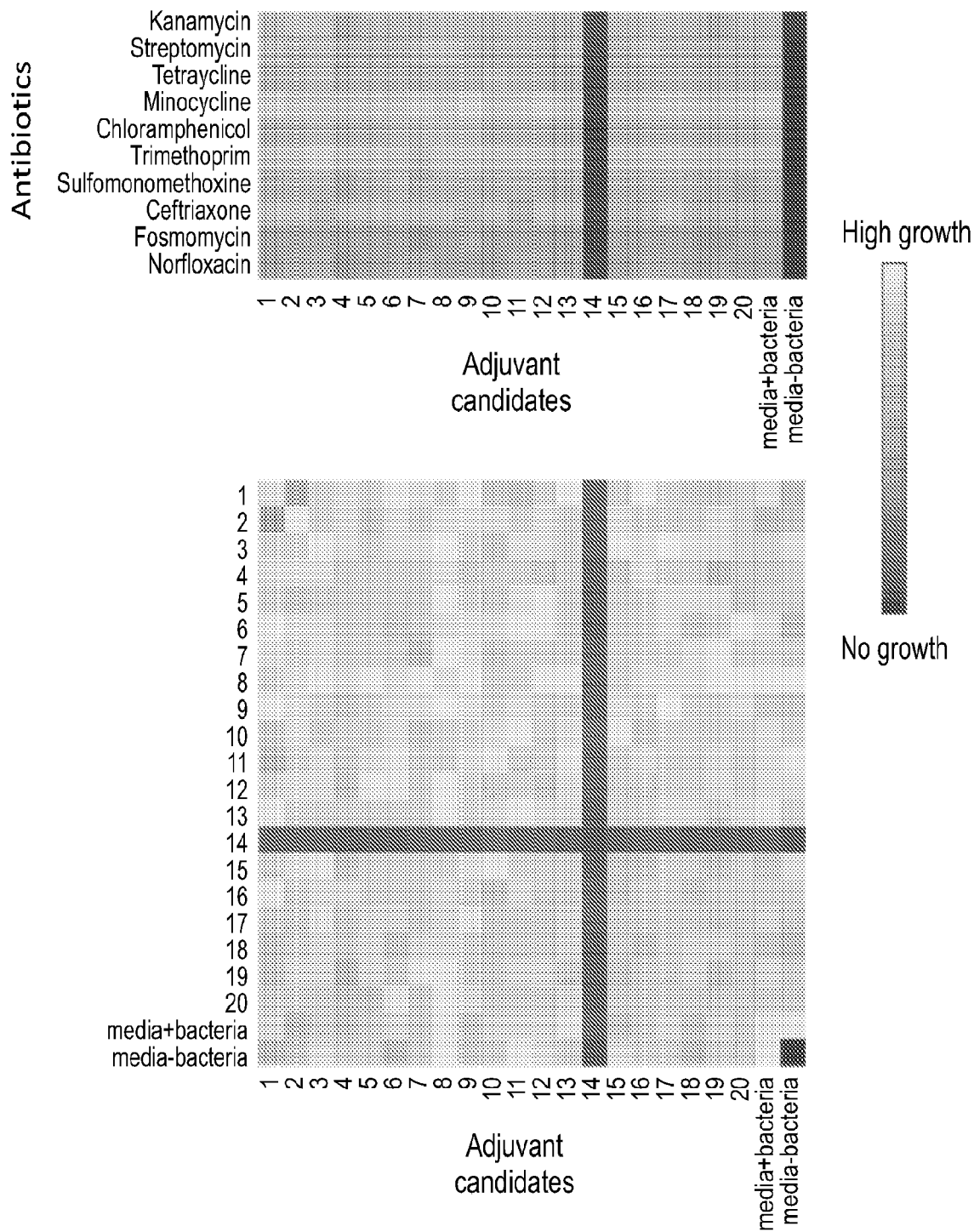
FIG. 20 is a set of heat maps showing the results of an antibiotic/adjuvant screen and pair-wise adjuvant screen according to example methods disclosed herein.

To test for adjuvant effects, droplets carrying 20 adjuvant candidates from a drug library of clinical candidates and bacteria were merged with droplets carrying 10 antibiotics. The results are show in FIG. 20. Growth effects are compared to a control containing the same media, but without adjuvants (column media+bacteria). Adjuvant 14 was detected to enhance all antibiotics, but was later discovered to have independent antibacterial activity. The same experiment also examined growth inhibition from all pairwise combinations of the adjuvants. None of the pairs led to statistically significant growth inhibition compared to the positive control (media+bacteria), although the experiment revealed one adjuvant (14) has antibacterial activity.

All publications, patents, and patent applications mentioned herein are incorporated by reference to the same extent as if each individual publication, patent or patent application was specifically and individually indicated to be incorporated by reference in its entirety. In the event of there being a difference between definitions set forth in this application and those in documents incorporated herein by reference, the definitions set forth herein control.

Various modifications and variations of the described methods, pharmaceutical compositions, and kits of the disclosure will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A microfluidic device comprising:
   at least one droplet input means for receiving one or more sets of droplets, each set of droplets comprising one or more agents;
   one or more arrays of microwells for receiving one or more droplets from the one or more sets of droplets, each microwell is in the shape of two or more interconnected hemispheres; and
   one flow channel located beneath each of the one or more arrays of microwells such that flow of a carrier fluid through the device occurs below the one or more arrays of microwells.

2. The microfluidic device of claim 1, comprising;
   oil carrier fluid within the flow channel to allow-droplets from each droplet set to be randomly distributed into the one or more arrays of microwells such that droplets from each droplet set are randomly co-located in individual microwells of the one or more arrays;
   a loading mechanism, wherein the loading mechanism comprises a bottom clamp on which the array of microwells is placed, one or more removable spacers that when inserted define the flow channel beneath the one or more arrays of microwells, a top clamp, and one or more connectors for securing the top clamp to the bottom clamp such that the one or more arrays of microwells is secured against the spacer when inserted or the bottom clamp when the spacers are removed; or
   both the oil carrier fluid within the flow channel and the loading mechanism.

3. The microfluidic device of claim 2, further comprising droplets, wherein the droplets rise or sink via buoyancy from the carrier oil in the flow channel into empty microwell spaces.

4. The microfluidic device of claim 1, wherein the microwells are sized to capture at least two droplets, at least three droplets, at least three droplets, at least four droplets, at least five droplets, or at least six droplets.

5. The microfluidic device of claim 1, wherein each microwell is sized to capture droplets of a same size or each microwell is sized to capture droplet of a different size.

6. The microfluidic device of claim 1, wherein the interconnected hemispheres are arranged in a linear fashion, or wherein the interconnected hemispheres are arranged in a radial fashion.

7. The microfluidic device of claim 1, wherein the device comprises a single flow channel.

8. The microfluidic device of claim 2, wherein the flow channel is approximately 10 mm to approximately 50 mm in width; or approximately 25 mm to approximately 100 mm in length; or approximately 100 μm to 500 μm in depth/height.

9. The microfluidic device of claim 1, further comprising a coalescing mechanism means for merging the two droplets in a microwell space to form a single droplet.

10. The microfluidic device of claim 9, wherein the coalescing mechanism coalesces the droplets by electrocoalescence, thermal coalescence, acoustic coalescence, changes in surfactant concentration, or a combination thereof.

11. A system comprising:
microfluidic device of claim 1; and
an automated high content imaging device means to image each microwell.

12. The microfluidic device of claim 6, wherein the microwells sized to hold between two and ten droplets, the droplets sized between 10 pL and 10 nL.

* * * * *

UNITED STATES PATENT AND TRADEMARK OFFICE
CERTIFICATE OF CORRECTION

PATENT NO. : 10,981,167 B2
APPLICATION NO. : 15/559381
DATED : April 20, 2021
INVENTOR(S) : Paul Blainey, Anthony Kulesa and Jared Kehe Page 1 of 1

It is certified that error appears in the above-identified patent and that said Letters Patent is hereby corrected as shown below:

In the Specification

Column No. 5, Line No. 55, "300 µM" should be -- 300 µm --
Column No. 10, Line No. 54, "cirucits"" should be -- circuits" --

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*